US008841279B2

(12) United States Patent
Taylor et al.

(10) Patent No.: US 8,841,279 B2
(45) Date of Patent: Sep. 23, 2014

(54) OLIGO-GULURONATE AND GALACTURONATE COMPOSITIONS

(75) Inventors: Catherine Taylor, Trondheim (NO); Kurt Ingar Draget, Trondheim (NO); Olav Asmund Smidsrod, Trondheim (NO)

(73) Assignee: Norwegian University of Science and Technology, Trondheim (NO)

( * ) Notice: Subject to any disclaimer, the term of this patent is extended or adjusted under 35 U.S.C. 154(b) by 531 days.

(21) Appl. No.: 12/595,818

(22) PCT Filed: Apr. 11, 2008

(86) PCT No.: PCT/GB2008/001287
§ 371 (c)(1),
(2), (4) Date: Feb. 4, 2010

(87) PCT Pub. No.: WO2008/125828
PCT Pub. Date: Oct. 23, 2008

(65) Prior Publication Data
US 2010/0152122 A1   Jun. 17, 2010

(30) Foreign Application Priority Data
Apr. 12, 2007   (GB) .................................. 0707096.4

(51) Int. Cl.
*A61K 31/715* (2006.01)
*A61K 31/70* (2006.01)
*A61K 45/06* (2006.01)

(52) U.S. Cl.
CPC ............... *A61K 45/06* (2013.01); *A61K 31/715* (2013.01)
USPC ............... 514/54; 514/23; 514/61; 536/123.1

(58) Field of Classification Search
USPC .............................. 514/54, 23, 61; 536/123.1
See application file for complete search history.

(56) References Cited

U.S. PATENT DOCUMENTS

| | | | |
|---|---|---|---|
| 4,225,592 A | 9/1980 | Lakatos et al. | |
| 5,166,137 A * | 11/1992 | Otterlei et al. | .................. 514/23 |
| 5,459,054 A | 10/1995 | Skjak-Braek et al. | |
| 5,460,957 A | 10/1995 | Hiura et al. | |
| 5,683,991 A | 11/1997 | Guggenbichler et al. | |
| 5,759,572 A | 6/1998 | Sugimoto et al. | |
| 5,795,587 A | 8/1998 | Gao et al. | |
| 6,121,441 A | 9/2000 | Simensen et al. | |
| 6,339,075 B1 | 1/2002 | King et al. | |
| 6,407,226 B1 | 6/2002 | Simensen et al. | |
| 6,440,413 B1 | 8/2002 | Hooreman | |
| 6,747,015 B2 | 6/2004 | Byon et al. | |
| 2003/0013678 A1 | 1/2003 | Lang et al. | |
| 2003/0022863 A1 | 1/2003 | Stahl et al. | |
| 2003/0059474 A1 | 3/2003 | Scott et al. | |
| 2003/0224070 A1 | 12/2003 | Sweazy et al. | |
| 2004/0073964 A1 | 4/2004 | Ellington et al. | |
| 2004/0224922 A1 | 11/2004 | King | |
| 2005/0158392 A1 | 7/2005 | Kim et al. | |
| 2006/0083780 A1 | 4/2006 | Heyes et al. | |
| 2009/0010914 A1 | 1/2009 | Taylor et al. | |

FOREIGN PATENT DOCUMENTS

| | | |
|---|---|---|
| CA | 2 428 473 A1 | 5/2002 |
| DE | 268865 A1 | 6/1989 |
| DE | 19520743 A1 | 12/1996 |
| EP | 324720 A1 | 7/1989 |
| EP | 506325 A1 | 9/1992 |
| EP | 0888778 A1 | 1/1999 |
| EP | 1234584 A1 | 8/2002 |
| EP | 1714660 A1 | 10/2006 |
| EP | 1745705 A1 | 1/2007 |
| EP | 1837018 A1 | 9/2007 |
| FR | 7576 M | 1/1970 |
| GB | 1042379 A | 9/1966 |
| GB | 2 430 881 A1 | 4/2007 |
| JP | 61-076413 | 4/1986 |
| JP | 01-197431 | 8/1989 |
| JP | 09208472 A | 8/1998 |
| JP | 2000-034302 | 2/2000 |
| JP | 2002-338493 A | 11/2002 |
| JP | 2005-145885 | 6/2005 |
| JP | 2006-028041 | 2/2006 |
| WO | WO 88/09794 A1 | 12/1988 |
| WO | WO 91/07951 A1 | 6/1991 |
| WO | WO 91/11205 A1 | 8/1991 |
| WO | WO 95/18145 A1 | 7/1995 |

(Continued)

OTHER PUBLICATIONS

Aikiyama, Hisayoshi et al. (1991) "Effect of Depolymerized Alginates on the Growth of Bifidobacteria" *Biosci. Biotech. Biochem* 56: 355-356.

Chono, S. et al. 2008 "An efficient and low immunostimulatory nanoparticle formulation for systemic siRNA delivery to the tumor" *Journal of Controlled Release* 131: 64-69.

Dalby, B. et al. 2004 "Advanced transfection with Lipofectamine 2000 reagent: primary neurons, siRNA, and high-throughput applications" *Methods* 33: 95-103.

Eiselt, Petra et al. (2000) "Porous carriers for biomedical applications based on alginate hydrogels" *Biomaterials* 21: 1921-1927.

(Continued)

*Primary Examiner* — Shaojia Anna Jiang
*Assistant Examiner* — Michael C Henry
(74) *Attorney, Agent, or Firm* — Knobbe Martens Olson & Bear, LLP (57) ABSTRACT

The invention provides a pharmaceutical composition comprising a macromolecular drug and an oligoguluronate or oligogalacturonate, e.g., having a number average degree of polymerization in the range 5 to 18, a guluronate (or galacturonate) fraction ($F_G$) of at least 0.80, a mannuronate fraction ($F_M$) of no more than 0.20, and having at least 95% mole with a degree of polymerization less than 20. The composition may be used in a method of treatment which comprises administering the composition to a mucosal surface in a human or non-human vertebrate subject.

16 Claims, 4 Drawing Sheets

(56) References Cited

FOREIGN PATENT DOCUMENTS

| WO | WO 98/13024 A2 | 4/1998 |
|---|---|---|
| WO | WO 01/15672 A2 | 3/2001 |
| WO | WO 01/17506 A1 | 3/2001 |
| WO | WO 01/66084 A2 | 9/2001 |
| WO | WO 01/72278 A2 | 10/2001 |
| WO | WO 2007/002224 A2 | 1/2004 |
| WO | WO 2005/089722 A1 | 9/2005 |
| WO | WO 2007/002224 A2 | 1/2007 |
| WO | WO 2007/039754 A1 | 4/2007 |
| WO | WO 2007/039760 A2 | 4/2007 |
| WO | WO 2007/046719 A2 | 4/2007 |
| WO | WO 2008/125828 A2 | 10/2008 |
| WO | WO 2008/137114 A1 | 11/2008 |
| WO | WO 2009/142892 A2 | 11/2009 |

OTHER PUBLICATIONS

Fiel, Stanley B. et al. (1995) "Comparison of Three Jet Nebulizer Aerosol Delivery Systems Used to Administer Recombinant Human DNase I to Patients With Cystic Fibrosis" *Chest Official Publication of the American College of chest Physicians* 108: 153-156.

Jiang, G. et al. 2007 "DNA/PEI/Alginate polyplex as an efficient in vivo gene delivery system" *Biotechnology and Bioprocessing Engineering* 12: 684-689.

Klöck, G. et al. 1997 "Biocompatibility of mannuronic acid-rich alginates" *Biomaterials* 18: 707-713.

Kong, H. J. et al. 2008 "Design of Biodegradable Hydrogel for the Local and Sustained Delivery of Angiogenic Plasmid DNA" *Pharaceutical Research* 25: 1230-1238.

Krebs, M. D. et al. 2009 "Localized and Sustained Delivery of Silencing RNA from Macroscope Biopolymer Hydrogels" *Journal of the American Chemical Society* 131: 9204-9206.

Pandey, Rajesh & Khuller, G.K. (2005) "Chapter 27: Alginate as a Drug Delivery Carrier" *Handbook of Carbohydrate Engineering* pp. 799-815.

Rakkhithawatthana, V. et al. 2010 "Investigation of gene transferring efficacy through nano-polyplex consisting of methylated N-(4-pyridinylmethyl) chitosan chloride and poly(ethylenimine) in human cell lines" *Carbohydrate Polymers* 80: 276-284.

Sioud, M. et al. 2003 "Cationic liposome-mediated delivery of siRNAS in adult mice" *Biochemical and Biophysical Research Communications* 312: 1220-1225.

Tadashi, Yoshimatsu et al. (2002) "Effects on Intestinal Flora of a Beverage Containing Non-fermentable Depolymerized Sodium Alginate and Water-soluable Fermentable Corn Bran Fiber" *The Journal of Nutrition and Dietetics* 60: 137-143.

Terada, A. et al. (1995) "Effect of Dietary Alginate on the Faecal Microbiota and Faecal Metabolic Activity in Humans" *Microbial Ecology in Health and Disease* 8: 259-266.

Yun, Y. H. et al 2004 "Hyaluronan microspheres for sustained gene delivery and site-specific targeting" *Biomaterials* 25: 147-157.

Westedt, U. et al. 2007 "Poly(vinylalcohol)-graft-poly(lactide-co-glycolide) nanoparticles for local delivery of paclitaxel for restenosis treatment" *Journal of Controlled Release* 119: 41-51.

Banning, D. et al. 1997 "Oscillatory and thermorheological characterisation of alginate/mucin mixes" *British Pharmaceutical Conference 1997* in *Pharmacy and Pharmacology* 49(4):40.

Murata, K. et al. 1992 "Continuous depolymerisation of alginates by a non-support bioreactor system containing flocculated bacterial cells" *J Fermentation and Bioeng.* 73(2):172-174.

Tang, J.X. et al. 2005 "Anionic poly(amino cid)s dissolve F-actin and DNA bundles, enhance DNase activity, and reduce the viscosity of cystic fibrosis sputum" *Am J Physiol Lung Cell Mol Physiol.* 289(4):L599-605.

Iwamoto, M. et al. 2005 "Structure—activity relationship of alginate oligosaccharides in the induction of cytokine production from RAW264.7 cells" *FEBS Letters* 579: 4423-4429.

Witschi, C. et al. 1999 "In vitro evaluation of microparticles and polymer gels for use as nasal platforms for protein delivery" *Pharmaceutical Research* 16: 382-390.

Hanninen, A. and Harrison, L.C. 2004 "Mucosal Tolerance to Prevent Type 1 Diabetes: Can the Outcome Be Improved in Humans?" *Rev Diabet Stud* 1: 113-121.

Merck Manual, "Disorders," www.merckmanuals.com/professional/index.html, accessed Aug. 6, 2012.

Merck Manual, "Diseases," www.merckmanuals.com/professional/index.html, accessed Aug. 6, 2012.

Merck Manual, "Diabetes," www.merckmanuals.com/professional/index.html, accessed Aug. 6, 2012.

Grasdalen, H et al. 1979 "A P.M.R. study of the composition and sequence of urinate residues in alginates" *Carbohydrate Research* 68: 23-31.

FMC Biopolymer 2003 "A world of possibilities lies just below the surface: Alginates" Brochure (in 20 pages).

Ikeda, A. and Ono T.H. 2000 "Preparation of low-molecular weight alginic acid by acid hydrolysis" *Carbohydrate Polymers* 42: 421-425.

Shidrawi, R.G.et al. 2002;"Emergency colonoscopy for distal intestinal obstruction syndrome in cystic fibrosis patients", *Gut*; 51: 285-286.

Shraishi, S. et al. J., 1991: "Improvement of Absorption Rate of Indomethacin and Reduction of Stomach Irritation by Alginate Dispersions" *J Pharm. Pharmacol* 43: 615-620.

\* cited by examiner

OLIGO-GULURONATE AND GALACTURONATE COMPOSITIONS

RELATED APPLICATIONS

This application is a U.S. National Phase of International Application No.: PCT/GB2008/001287, filed Apr. 11, 2008, designating the U.S. and published in English on Oct. 23, 2008 as WO 2008/125828, which claims the benefit of Great Britain Application No. 0707096.4, filed Apr. 12, 2007.

This invention relates to oligo-guluronate and galacturonate compositions, and to a method of treatment of human or non-human animals, in particular mammals, with oligoguluronates or oligogalacturonates, e.g. to combat elevated mucosal viscosity, e.g. to enhance mucus clearance, especially from the respiratory tract, in particular the sinuses and the lungs, in particular in the treatment of cystic fibrosis (CF) and sinusitis.

Cystic fibrosis is the most common lethal genetic disease in European populations. The disease is caused by a mutation in the gene that codes for the cystic fibrosis transmembrane regulator (CFTR), a chloride channel that is present in secretary and other cells in the body. The disease is characterized by the presence of thick, intractable mucus secretions in the body that can lead to lung disease, digestive problems and infertility. The normal pattern of mucociliary clearance in the lungs fails to clear the unduly viscous mucus which becomes colonized by microorganisms, which in turn increases mucus viscosity and may lead to chronic lung inflammation and obstruction. Lung disease is thus the biggest health problem for the majority of CF patients and is the major cause of death.

Mucus is a normal secretion of the entire respiratory tract, including the lungs. Its primary function is as part of the mucociliary clearance system that keeps the lungs clean and protects against infection. The mucociliary clearance system has three main components: mucus; cilia; and the airway surface liquid. The epithelial surface thus comprises mucus secreting goblet cells and ciliated epithelial cells with an overlying layer of airway surface liquid and above that a layer of mucus, into which the tips of the cilia protrude. The mucus is a sticky gel material composed primarily of water (about 95% wt.) and mucins, gel forming molecules responsible for the physical properties of the mucus. The cilia are small hair-like projections from the surface of the epithelial cells, which beat rhythmically in the watery, non-viscous airway surface liquid with their tips immersed in the mucus layer. The mucus layer forms a sticky blanket on the lung surface that traps bacteria, viruses, inhaled particles, environmental pollutants and cell debris. The beating of the cilia serves to propel this mucus blanket and anything trapped in it towards the mouth and out of the lungs. Under normal conditions, the mucociliary clearance system functions effectively and the lungs are kept clean and free of infection. If the system is overwhelmed, there is a second line of defence—cough. Thus when increased levels of mucus are secreted in response to irritation or inflammation, e.g. due to inhaled particles or infection, the mucus is projected out of the lungs by the cough reflex.

In CF patients the mucus in the lung is thicker and more viscous than normal, and this thicker mucus is not so easily transported by the cilia. As a result the mucociliary clearance system is compromised and the lungs are more vulnerable to infection. In addition, the lungs of CF patients appear to be in a hyper-inflammatory state with a continual low level of inflammation and a heightened response to agents that normally cause inflammation. This is problematic as part of the response to inflammation is increased production of mucus. The increased mucus builds up if it is too thick to be cleared by the mucociliary clearance system or coughing, lung capacity is reduced and the exchange of oxygen across the mucosa is decreased. This provides an ideal environment for bacterial colonisation, a serious problem for CF patients as it also causes inflammation and activates the immune response. This leads not only to increased mucus secretion but also an increased presence of immune response cells and agents such as macrophages and lysozymes. As bacteria and macrophages die, their cell contents are released into the mucus and these include viscous molecules such as DNA. Furthermore, some of the bacteria, e.g. *Burkholdia* sp. and *Pseudomonas aeruginosa*, also secrete highly viscous polysaccharides, in the latter case alginates. These molecules further increase the viscosity of the mucus, in the case of the alginates apparently by interaction with the mucin matrix of the mucus but in the case of DNA apparently by increasing the viscosity of the sol phase within the mucin matrix.

Maintaining the mucus in a form capable of being transported by the cilia is thus a key goal of treatment of CF. Agents which simply break down its gel-like structure would result in fluid which was as untransportable as the hyperviscous mucus of the CF patient. It is important therefore that any treatment agent should not break down the gel matrix formed by the glycoprotein mucins.

We have found that this can be achieved using oligoguluronates or oligogalacturonates (preferably oligoguluronates) having a number average degree of polymerization ($DP_n$) in the range 5 to 30, preferably 5 to 18.

Elsewhere in the body, for example the ears, the cervix and especially the respiratory tract, in particular in the sinuses, especially the paranasal sinuses, overly viscous mucous can present problems. The oliguluronates and oligogalacturonates can also be used to address these problems.

Cervical mucus, produced by the glands of the uterine cervix, is a heterogeneous entity containing different types of secretions in different proportions throughout the menstrual cycle. The nature of the secretion is such that it provides a barrier to sperm migration through the cervix at all times except during the "fertile window" when ovulation is occurring and conception is possible. This acts to protect the uterus, fallopian tubes and ovaries from unnecessary exposure to pathogens.

In order to support sperm migration during the fertile window, the cervical mucus must have appropriate biochemical and biophysical characteristics. Biochemical properties, such as pH and osmolality are important in providing appropriate conditions for sperm survival (see Marriott et al., "Mucus physiology and pathology" in Bioadhesive Drug Delivery Systems, CRC Press, 1990), while the biophysical properties, such as rheology and macromolecular network morphology, affect the motility of sperm within the mucus (see Rutllant et al., Reprod. Dom. Anim. 40: 79-86 (2005)).

Clinically, the fertile window may be identified by detecting the surge in lutenising hormone before ovulation and the rise in basal body temperature after ovulation and by examining the biophysical properties of the cervical mucus in particular its spinnbarkeit (spinnability), which is essentially a measure of how stretchy the mucus is and as such is related to the rheology of the mucus. Cervical mucus ferning, i.e. the crystallisation patterns that form when mucus from the ovulatory period is allowed to air dry, has also been shown to be related to the morphology of the macromolecular network within the mucus (see Menarguez et al., Human Reproduction 18: 1782-1789 (2003)).

The ferning patterns of mucus (and hence the macromolecular network morphology) have been shown to be a significant factor in the chance of achieving a pregnancy with the use of artificial insemination and for a subset of women, "problem mucus" appears to be a major barrier to achieving pregnancy (see Boyers et al., Human Reproduction 6: 1108-1114 (1991)).

There is therefore a need for a method of modulating the biophysical properties of cervical mucus for optimum sperm motility, not just for women with "problem mucus" but for any woman who wishes to maximise her chances of conceiving, and also for animal breeders who wish to maximise the chance of pregnancy in their animals.

We have found that this can be achieved using oligoguluronates or oligogalacturonates (preferably oligoguluronates) having a number average degree of polymerization ($DP_n$) in the range 5 to 30, preferably 5 to 18.

These uses of oligoguluronates and oligogalacturonates are described for example in WO2007/039754 and WO2007/039760, the contents of which are hereby incorporated by reference.

The oligoguluronates and oligogalacturonates (hereinafter "G-blocks") may be prepared from natural polysaccharides as described below and comprise a mixture of compounds of different degrees of polymerization (DP). We have now found that by removing the high molecular weight "tail" of the G-block mixture, a material with improved characteristics in terms of its ability to modify the structure of mucus is obtained.

The claims hereto thus set forth particularly preferred values for number average degree of polymerization ($DP_n$), guluronate/galacturonate fraction ($F_G$), mannuronate fraction ($F_M$) and molecular weight distribution.

We have also surprisingly found that G-blocks (especially oligoguluronates) may advantageously be used to facilitate uptake from mucosal surfaces of macromolecular drugs, i.e. drugs having a molecular weight above 2000 Da (preferably above 4000 Da, for example 5-2000 kDa) when they are co-administered. This effect has been clearly demonstrated using a Madin-Darby canine kidney (MDCK) cell model.

Thus viewed from one aspect the invention provides a pharmaceutical composition comprising an oligoguluronate or oligogalacturonate and a macromolecular drug.

Viewed from a further aspect the invention provides a method of treatment of a human or non-human vertebrate (e.g. mammalian, avian or reptilian, especially mammalian) subject which comprises administering to said subject a pharmaceutical composition comprising an effective amount of a macromolecular drug, the improvement comprising coadministering said drug to a mucosal surface of said subject with an effective amount of an oligoguluronate or oligogalacturonate.

Viewed from another aspect the invention provides the use of an oligoguluronate or oligogalacturonate for the manufacture of a medicament further comprising a macromolecular drug for use in a method of treatment which comprises administering said medicament to a mucosal surface in a human or non-human vertebrate subject.

By mucosal surface is meant for example the interior of the nose, the vagina, the lungs, the lining of the mouth (e.g. under the tongue) or the anus. Administration into the mouth will generally be by inhalation of a spray or placement sublingually or by retention in the mouth. Administration orally into the gastrointestinal tract for drug uptake in the stomach or intestines is one further option but is less preferred since the macromolecular drugs are frequently liable to destruction if so administered.

Examples of suitable macromolecular drugs include nucleic acids (e.g. DNA or RNA), proteins, peptides, hormones, antibodies, etc, more particularly insulin, anti-TNF (e.g. etanercept, infliximab, adalinumab, etc), interferon (e.g. interferon alpha or beta), factor VII, factor VIIa, factor VIII, factor IX, follicle stimulating hormone, erythropoietin, trastuzumab, rituximab, granulocyte colony stimulating factor (and PEGylated equivalents), growth hormones such as somatotropin, apotransferrin (used in the treatment of atransferrinemia), and beta-glucocerebosidase. Most of these have such poor biological uptake from mucosal surfaces that they are conventionally administered by injection, an administration route which is less pleasant for the patient than mucosal surface administration. In the method of the invention such drugs can of course be used for their normal indications. The appropriate dosage may readily be determined from animal models working on the basis that the quantity taken up should be comparable to the conventional injected dose. If desired, the compositions of the invention may be administered subcutaneously or intramuscularly; however, this is less preferred and iv injection is generally undesirable.

Examples of suitable macromolecular drugs suitable for incorporation in the compositions of the invention include the anti-TNF drugs sold under the trade names Enbrel and Remicade; the anti-CD20 sold under the trade name Rituxan; the erythropoietins sold under the trade names Procrit, Eprex, Aranesp, Epogen, NeoRecormon, and Epogin; the G-CSF sold under the trade name Neulasta; the ant-EGFR sold under the trade name Herceptin; the interferons sold under the trade names Avonex, Rebif, Betaseron, Neupogen and Pegasys; the factor VIII sold under the trade name Kogenate; the factor VII sold under the trade name NovoSeven; the factor IX sold under the trade name Benefix; the growth hormones sold under the trade names Genotropin and Nutropin; the tPA sold under the trade name Activase; the FSH sold under the trade name Follistim; and the glucocerebrosidase sold under the trade name Cerezyme. The manufactures' websites give details of indications and dosages.

The macromolecular drug may of course be a nucleic acid for use in gene therapy.

The macromolecular drug is preferably one with a desired physiological effect beyond simply any effect of reducing infection, inflammation, mucosal viscosity or other lung problems. In particular it is preferably other than a nucleic acid cleaving enzyme, gelsolin, dextran, polyASP or polyGLU.

Macromolecular drugs sometimes have a tendency to form aggregates in aqueous solution and, while not wishing to be bound by theory, it is thought that part of the improved uptake achieved by coadministration of G-blocks is a result of the effect of the G-blocks in reducing aggregate formation. The invention is thus especially suitable for use with macromolecules, like insulin, which have this tendency to aggregate. A further part of the improved uptake achieved by coadministration of G-blocks is thought to lie in the ability of the G-blocks to promote passage through glycocalyx structures on the cell surfaces—this may arise by virtue of the G-blocks facilitating access by the macromolecular drug to the appropriate cell surface receptors.

The G-block used is preferably a physiologically tolerable oligoguluronate or oligogalacturonate having a number average degree of polymerization in the range 5 to 18 (especially 7 to 15), a guluronate (or galacturonate) fraction ($F_G$) of at least 0.80 (preferably at least 0.85, especially at least 0.92), a mannuronate fraction ($F_M$) of no more than 0.20 (preferably no more than 0.15, especially no more than 0.08), and having at least 95% mole with a degree of polymerization less than 20 (preferably less than 17). The G-block is preferably present in the compositions at 0.1-50 mg/mL, especially 0.5-

25 mg/mL, particularly 1-10 mg/mL in aqueous solution when ready to use. Alternatively expressed, the G-block and the macromolecular drug are preferably present in a relative weight ratio of about 0.5:1 to 10:1, particularly about 1:1.

Viewed from another aspect the invention provides a method of treatment of a human or non-human vertebrate (e.g. mammalian, avian or reptilian, especially mammalian) subject to reduce mucosal viscosity on a mucosal surface in said subject and in particular to combat mucosal hyperviscosity (e.g. to treat glue ear, sinusitis, or cystic fibrosis, to enhance the likelihood of impregnation following insemination or intercourse, to enhance drug delivery across mucosal surfaces), which method comprises application to said mucosal surface of an effective amount of a physiologically tolerable oligoguluronate or oligogalacturonate having a number average degree of polymerization in the range 5 to 18, a guluronate (or galacturonate) fraction ($F_G$) of at least 0.92, a mannuronate fraction ($F_M$) of no more than 0.08, and having at least 95% mole with a degree of polymerization less than 20.

Where the oligoguluronate or oligogalacturonate is being applied to a mucosal surface in the respiratory tract (i.e. the nose, sinuses and the lungs) or in the ears, it will preferably be formulated in aqueous solution at a concentration of 40 to 140 mg/mL (calculated on the basis of the weight of the oligoguluronate or oligogalacturonate in sodium salt form, hereinafter referred to as "sodium salt basis"). Where it is administered into the lungs, the daily dosage for a human will be 100 to 2000 mg/day for an adult (sodium salt basis), preferably 120 to 1000 mg/day, especially 150 to 500 mg/day. For a child the dosage may be proportional the child's bodyweight assuming an adult bodyweight of 70 kg for the above dose ranges. This daily dosage will preferably be given in 2, 3 or 4 temporally spaced applications.

Where the oligoguluronate or oligogalacturonate is being applied to a mucosal surface in the vagina or is being applied rectally, it may also be presented in a form other than an aqueous solution. Thus for example it may be in tablet, coated tablet (especially delayed or sustained release coated tablet), capsule, suppository, pessary, gel, emulsion, syrup, dispersion, suspension, emulsion, powder, cream, paste, etc. form. For this purpose it may be formulated with conventional pharmaceutical carriers and excipients and the dosage form may be prepared in conventional fashion.

For vaginal application, the oligouronate (ie oligoguluronate or oligogalacturonate) is preferably applied in the form of a sterile aqueous composition, e.g. a solution, gel, emulsion, cream or paste, or as a tablet, capsule or vaginal suppository. However gel forms, especially aqueous lubricant gels, are preferred Such compositions, which will be spermicide-free, may if desired contain further agents to enhance sperm function, e.g. pH regulators and antioxidants, or to assist insemination, e.g. muscle relaxants, lubricants, etc. Clearly the compositions may also contain further physiologically tolerable pharmaceutical or cosmetic components such as are normally found in compositions for vaginal application, e.g. binders, diluents, soluble capsule shells, fragrances, antibiotics, vitamins, oils, emulsifiers, suppository bases, etc.

The oligouronate will preferably be present as about 0.1 to 2.5 g per dosage unit, more preferably 0.5 to 2 g/dosage unit for an adult human female. Dosages for other species may be calculated analogously by reference to average body size, e.g. [(0.1 to 2.5)/60] g/dosage unit/kg bodyweight, etc.

The composition is preferably applied in advance of insemination, e.g. 1 to 60 hours beforehand, preferably 2 to 48 hours beforehand, especially 4 to 36, e.g. 20 to 52 hours beforehand. This may be achieved for example by vaginal douche, by vaginal insertion of a water-degradable tablet or capsule, or by injection of a gel or paste. The timing of application may be selected by monitoring parameters indicative of ovulation or proximity of ovulation, e.g. temperature.

If desired, the composition may be applied two or more times, e.g. well in advance of insemination and shortly before (e.g. within 1 hour of) insemination.

Where a pH regulator is included in the composition, this is preferably such as to cause the vaginal pH to become slightly basic, e.g. pH 7.1 to 7.6, especially about pH 7.4. Routine physiologically tolerable buffers may be used in this regard.

The female treated according to the method of the invention is preferably a human female, in particular one diagnosed as having fertility problems due to problematic mucus. The method however may be used by other female humans of an age capable of becoming pregnant in order to increase the chance of pregnancy. It may also be used by vets and animal breeders, e.g. farmers, for animals such as cows, horses, dogs, cats, sheep, goats, pigs, etc.

The compositions of the invention for vaginal application are preferably packaged together with instructions for use in the method of the invention, particularly preferably in dosage unit form, and especially preferably together with an applicator, e.g. a syringe. The use of pre-loaded syringes is especially preferred. Alternatively the applicator may take the form of a cervical diaphragm, loaded on the concave side with the composition, to be removed before insemination unless the diaphragm membrane is of a sperm-permeable or water-soluble material. Such syringes and diaphragms form further aspects of the present invention.

For administration into the gastrointestinal tract rectally, the daily dosage will typically be 0.1 to 100 mg/kg bodyweight, more preferably 1 to 50 mg/kg, especially 1.5 to 25 mg/kg (sodium salt basis). Administration is preferably once to four times daily.

For administration into the ears, the daily dosage will typically be 0.05 to 4 mg/kg bodyweight (sodium salt basis), more preferably 0.1 to 2 mg/kg. Administration is preferably effected once to four times daily.

The optimum dose may readily be determined by routine dosage ranging experiments, optionally following initial investigation of an animal model, e.g. a dog model.

The compositions of the invention may be produced using conventional pharmaceutical carriers and excipients, e.g. sterile solvents (such as water, especially water for injections), osmolality modifiers, flavours, pH regulators, etc. They may contain additional active components, for example agents which serve to break down biopolymers not involved in the mucin matrix of the mucus (e.g. DNase, particularly rhDNase), antibacterial agents, anaesthetics, and anti-inflammatories.

Combination therapy using a such further agent and the oligoguluronate or oligogalacturonate, administered separately or together is a particularly preferred embodiment of the method of the invention. Such further agents may be used in their normal doses or even at lower doses, e.g. 50% of normal dose.

The oligoguluronate or oligogalacturonate used according to the invention preferably has a number average degree of polymerization ($DP_n$) of from 7 to 15, more preferably 8 to 12, especially about 10. The molecular weight distribution is preferably such that no more than 5% mole has a degree of polymerization (DP) above 17, more preferably no more than 5% mole has a DP above 14, still more preferably no more than 5% mole has a DP above 12 (e.g. in each case above a DP two higher than the relevant upper limit for $DP_n$). Likewise it is preferred that no more than 5% mole has a DP below a number two smaller than the relevant lower limit for $DP_n$).

The counterion for the oligoguluronate or oligogalacturonate may be any physiologically tolerable cation, e.g. any of the physiologically tolerable ions commonly used for charged drug substances, e.g. sodium, potassium, meglumine, etc. Ions which promote alginate gelation, e.g. group 2 metals, however will preferably not be used. Sodium is generally preferred.

Thus viewed from a further aspect the invention provides a sterile sprayable aqueous liquid composition comprising an aqueous solution of a physiologically tolerable oligoguluronate or oligogalacturonate having a number average degree of polymerization in the range 5 to 18 (preferably 7 to 15, more preferably 8 to 12, especially about 10), a guluronate (or galacturonate) fraction ($F_G$) of at least 0.80 (preferably at least 0.85, more preferably at least 0.90, especially at least 0.92, most especially at least 0.95), a mannuronate fraction ($F_M$) of no more than 0.20 (preferably no more than 0.15, more preferably no more than 0.10, especially no more than 0.08, most especially no more than 0.05), and having at least 95% mole with a degree of polymerization less than 20 (preferably less than 17, more preferably less than 14), said solution containing said oligoguluronate at a concentration of 40 to 140 mg/mL, preferably 50 to 100 mg/mL, especially 55 to 75 mg/mL (sodium salt basis).

Viewed from a further aspect the invention provides a spray applicator comprising a reservoir and a droplet generator, said reservoir containing a sterile aqueous solution or composition according to the invention. Such spray applicators, and indeed the oligoguluronates or oligogalacturonates, may be used in the treatment of cystic fibrosis, sinus or nasal blockage, or congestion resulting from the common cold or other reasons.

The compositions intended for inhalation into the lungs desirably contain a further physiologically tolerable mucosal viscosity reducing agent, e.g. a nucleic acid cleaving enzyme (e.g. a DNAse such as DNase I), gelsolin, a thiol reducing agent, an acetylcysteine, sodium chloride, an uncharged low molecular weight polysaccharide (e.g. dextran), arginine (or other nitric oxide precursors or synthesis stimulators), or an anionic polyamino acid (e.g. poly ASP or poly GLU). The use of a DNase is especially preferred.

For administration into the lungs, the oligouronates may be in the form of powders, e.g. of approximately nanometer to micrometer (e.g. 10 to 50000 nm) mode particle size.

Viewed from a still further aspect the invention provides physiologically tolerable oligoguluronates or oligogalacturonates having a number average degree of polymerization in the range 7 to 15 (preferably 8 to 12), a guluronate (or galacturonate) fraction ($F_G$) of at least 0.92 (preferably at least 0.95), a mannuronate fraction ($F_M$) of no more than 0.08 (preferably no more than 0.05), and having at least 95% mole with a degree of polymerization less than 17 (preferably less than 14) for use in medicine.

Viewed from a still further aspect the invention provides the use of a physiologically tolerable oligoguluronate or oligogalacturonate having a number average degree of polymerization in the range 7 to 15 (preferably 8 to 12), a guluronate (or galacturonate) fraction ($F_G$) of at least 0.92 (preferably at least 0.95), a mannuronate fraction ($F_M$) of no more than 0.08 (preferably no more than 0.05), and having at least 95% mole with a degree of polymerization less than 17 (preferably less than 14) for the manufacture of a medicament for use in a method of medical treatment to reduce mucosal viscosity at a mucosal surface by application to said surface, e.g. in the treatment of cystic fibrosis, glue ear, sinusitis, chronic obstructive pulmonary disease (COPD, especially its wet forms), bronchitis, emphysema, impaired fertility, or to enhance drug delivery across a mucosal surface.

Viewed from a still further aspect the invention provides the use of a physiologically tolerable oligoguluronate or oligogalacturonate having a number average degree of polymerization in the range 7 to 15 (preferably 8 to 12), a guluronate (or galacturonate) fraction ($F_G$) of at least 0.85 (preferably at least 0.92), a mannuronate fraction ($F_M$) of no more than 0.15 (preferably no more than 0.08), and having at least 95% mole with a degree of polymerization less than 17 (preferably less than 14) for the manufacture of a medicament containing said oligoguluronate or oligogalacturonate in sterile aqueous solution at a concentration of 40 to 140 mg/mL (sodium salt basis) for use in a method of medical treatment to reduce mucosal viscosity at a mucosal surface by application to said surface, e.g. in the treatment of cystic fibrosis, glue ear, sinusitis, chronic obstructive pulmonary disease (COPD, especially its wet forms), bronchitis, emphysema, impaired fertility, or to enhance drug delivery across a mucosal surface.

Viewed from a yet still further aspect, the invention provides a method of treatment of a human or non-human vertebrate animal (eg mammalian, avian or reptilian, preferably mammalian) subject to reduce mucosal viscosity on a mucosal surface therein, which method comprises administering to said surface an effective amount of a physiologically tolerable oligoguluronate or oligogalacturonate having a number average degree of polymerization in the range 7 to 15 (preferably 8 to 12), a guluronate (or galacturonate) fraction ($F_G$) of at least 0.92 (preferably at least 0.95), a mannuronate fraction ($F_M$) of no more than 0.08 (preferably no more than 0.05), and having at least 95% mole with a degree of polymerization less than 17 (preferably less than 14).

Viewed from a yet still further aspect, the invention provides a method of treatment of a human or non-human vertebrate animal (eg mammalian, avian or reptilian, preferably mammalian) subject to reduce mucosal viscosity on a mucosal surface therein, which method comprises administering to said surface an effective amount of a sterile aqueous solution containing, at a concentration of 40 to 140 mg/mL (sodium salt basis), a physiologically tolerable oligoguluronate or oligogalacturonate having a number average degree of polymerization in the range 7 to 15 (preferably 8 to 12), a guluronate (or galacturonate) fraction ($F_G$) of at least 0.85 (preferably at least 0.92), a mannuronate fraction ($F_M$) of no more than 0.15 (preferably no more than 0.08), and having at least 95% mole with a degree of polymerization less than 17 (preferably less than 14).

In the methods of the invention, administration to the mucosal surface may be direct, e.g. by insertion of a pessary, by injection of a vaginal gel, by injection or administration of drops into the ear or nose, or by inhalation of spray droplets into the nose or lungs, or indirect, e.g. by administration of a suppository or enema to reach the distal end of the gastrointestinal tract.

Viewed from another aspect the invention provides a method of treatment of a human or non-human vertebrate animal (eg mammalian, avian or reptilian, preferably mammalian) subject to combat mucosal hyperviscosity in the ears, sinus or lungs of said subject, which method comprises administering into the ears, nose or lungs of said subject an effective amount of a physiologically tolerable oligoguluronate or oligogalacturonate having a number average degree of polymerization in the range 5 to 18, a guluronate (or galacturonate) fraction ($F_G$) of at least 0.92, a mannuronate fraction ($F_M$) of no more than 0.08, and having at least 95% mole with a degree of polymerization less than 20, preferably in sterile aqueous solution at a concentration of 40 to 140 mg/mL (sodium salt basis).

The application of the oligouronate in this method may be by any means which delivers it to a mucus secreting, or mucus carrying surface in the patient's ears or respiratory tract, e.g. the paranasal sinuses or more preferably the lungs. Introduction will typically be by inhalation, e.g. of liquid droplets (for example an aerosol) or a powder, or by administration of drops into the nose or ears.

We have also found that oligoguluronates and oligogalacturonates may be used to enhance uptake across a mucosal surface of a physiologically active agent (hereinafter a "drug substance"). Thus viewed from a further aspect the invention provides a pharmaceutical composition comprising a drug substance and a physiologically tolerable oligoguluronate or oligogalacturonate having a number average degree of polymerization in the range 5 to 18, a guluronate (or galacturonate) fraction ($F_G$) of at least 0.80, a mannuronate fraction ($F_M$) of no more than 0.20, and having at least 95% mole with a degree of polymerization less than 20, preferably one of the oligouronates described above as preferred. Such compositions may take any conventional form, eg powders, tablets, capsules, solutions, suppositories, dispersions, etc, and may be produced in conventional fashion using conventional pharmaceutical carriers and excipients. The drug substance is preferably a charged molecule, especially a macromolecule (eg having a molecular weight above 2 kDa), for example a poly-electrolyte or ampholyte, in particularly a negatively charged molecule. Thus for example, the drug substance may be a complex macromolecule such as a glycoprotein, for example transferrin. Viewed from a further aspect the invention provides the use of a physiologically tolerable oligoguluronate or oligogalacturonate having a number average degree of polymerization in the range 5 to 18, a guluronate (or galacturonate) fraction ($F_G$) of at least 0.80, a mannuronate fraction ($F_M$) of no more than 0.20, and having at least 95% mole with a degree of polymerization less than 20, preferably one of the oligouronates described above as preferred, for the manufacture of a medicament further containing a drug substance for administration to a mucosal surface for the uptake of said drug substance therethrough. Viewed from a still further aspect the invention provides a method of treatment of a human or non-human vertebrate animal subject by the administration to a mucosal surface therein of an effective amount of a drug substance to combat a condition responsive to said drug substance, the improvement comprising administering said drug substance with a physiologically tolerable oligoguluronate or oligogalacturonate having a number average degree of polymerization in the range 5 to 18, a guluronate (or galacturonate) fraction ($F_G$) of at least 0.80, a mannuronate fraction ($F_M$) of no more than 0.20, and having at least 95% mole with a degree of polymerization less than 20, preferably one of the oligouronates described above as preferred. Administration will typically be nasal, by inhalation, rectal or vaginal. The drug substance will typically be used at from 50 to 110% of its normal dose.

While the oligouronate may be a synthetic material, it is preferably a derivative of a naturally occurring polysaccharide. It may be a single compound or it may be a mixture of oligouronate compounds, e.g. of a range of degrees of polymerization.

Oligouronates are readily accessible from natural sources since many natural polysaccharides are in block copolymer form containing blocks of guluronic acid residues (so-called G-blocks), frequently together with blocks of mannuronic acid residues (so-called M blocks). M-blocks or M/G-blocks can be used in place of G-blocks According to the invention; however this is not preferred.

Polysaccharide to oligosaccharide cleavage to produce oligouronates useable according to the present invention may be performed using conventional polysaccharide lysis techniques such as enzymatic digestion and acid hydrolysis. The use of acid hydrolysis however is preferred. Oligouronates of the desired $DP_n$ and molecular weight distribution may then be separated from the polysaccharide breakdown products chromatographically using an ion exchange resin, by fractionated precipitation or solubilization, or by dialysis.

Suitable polysaccharides are discussed for example in "Handbook of Hydrocolloids", Ed. Phillips and Williams, CRC, Boca Raton, Fla., USA, 2000. The use of alginates however is especially preferred as these naturally occur as block copolymers of mannuronic (M) and guluronic (G) acids and G-block oligomers can readily be produced from alginate source materials.

Where alginates are used as the starting material for preparation of the oligouronate, the guluronic acid content may if desired be increased by epimerization with mannouronan C-5 epimerases from *A. vinelandii*.

Oligoguluronates suitable for use according to the invention may conveniently be produced by acid hydrolysis of alginic acid from *Laminaria hyperborea*, dissolution at neutral pH, addition of mineral acid to reduce the pH to 3.4 to precipitate the oligoguluronate, washing with weak acid, resuspension at neutral pH and freeze drying.

The invention will now be described further with reference to the following non-limiting Examples and the accompanying drawings, in which.

EXAMPLE 1

Preparation of sodium oligoguluronate of $DP_n$ 5 to 18

1. A guluronate rich alginic acid (pH 2-3; 15-40% dry weight) from the stipe of *Laminaria hyperborea* is extensively hydrolysed with a mineral or organic acid, preferably HCl, at 70-100° C. for 2-12 hrs.
2. After hydrolysis, the pH of the oligosaccharide mixture is increased to 3-4 and it is washed with low ionic strength water to remove M-rich fragments and low molecular weight components.
3. If necessary, the purified oligosaccharide mixture is hydrolysed and purified further as in steps 1 and 2.
4. The purified oligosaccharide mixture is then neutralized with alkali, preferably NaOH or $Na_2CO_3$, to give soluble G-blocks and the dry weight content is adjusted to 2.5-20%.
5. To obtain a product with acceptable number average degree of polymerization as well as molecular weight distribution, the G-block solution is filtered twice. First through a filter with an approximate cut-off of 1000 Da to remove oligomers below DP 5. The retentate is then filtered through a filter with an approximate cut-off of 4000 Da to remove G-block fragments above approximately DP 20.
6. If necessary, the dry matter content of the resulting permeate is adjusted and the solution is spray-dried. The resulting off-white to light yellow powder (product) has a moisture content less than 15%.

EXAMPLE 2

Preparation of sodium oligoguluronate of $DP_n$ 7 to 15

The preparation steps are as follows:
1. As in Example 1 above.
2. As in Example 1 above.
3. As in Example 1 above.
4. To optimize the yield and purity, the dry matter content of the oligosaccharide mixture is adjusted to 5-15% the oligosaccharide mixture is solubilised in an acetic acid buffer (50-250 mM) to reach a final pH of the solution of 3.8-5.0.
5. The solubilised oligosaccharide in acetate buffer is further hydrolysed homogeneously at 70-100° C. for 1-15 hours to lower the content of high molecular weight fragments and increase the physiologically active G-block fragments.
6. Filtration (also including de-salting) and spray-drying is effected as described in steps 5 and 6 of Example 1 above.

Oligoguluronates may also be prepared as described in U.S. Pat. No. 6,121,441 and U.S. Pat. No. 6,407,226, the contents of which are hereby incorporated by reference. Indeed, the products of Examples 1 and 2 herein may advantageously be produced using an oligoguluronate produced according to U.S. Pat. No. 6,121,441 as the starting material.

EXAMPLE 3

Characterisation and Quality Control

For Examples 1 and 2, including for checking the intermediate products, the following techniques are used:

Purity (content of guluronic acid residues) and number average degree of polymerization is determined by $^1$H-NMR spectroscopy as described by Grasdalen et al in Carbohydr. Res. 68(1):23-31 (1979).

High precision anionic chromatography combined with pulse-amperiometric detection (HPAEC-PAD), commercialized by Dionex, is also used for the characterization of the oligomeric material. The following method is used for the characterization of G-blocks:
1. G-block samples are solubilised in MQ water, 1-2 mg/ml
2. 0.1 M NaOH solution (without carbonate) is used as mobile phase, and 1.0M sodium acetate is used as eluent. All solutions are de-gassed with helium and filtered through a 0.22 micrometer filter
3. 20 microliter samples are injected, and a AG4A pre-column and a IonPac 4×250 AS4A main column are employed.
4. The columns are eluted with a linear gradient from 0 to 87.5% NaAcetate in 0.1 M NaOH within 90 minutes. Elution speed is 1 ml/min at a pressure regime of 650-750 psi.
5. After determining the response factor as function of chain length, the concentration of each oligomer can be calculated, implying that both the number and the weight average molecular weight as well as the molecular weight distribution can be determined.

Possible further treatment of the oligosaccharide: this consideration, i.e. if the relevant parameters are outside the desired ranges, is linked to the yield of manufacturing of the product. It is no problem to have any hydrolysate product of a high-G alginate to fit within the required parameter ranges, but the yield may be low. In order to optimize yield and still be within the required parameter ranges, the following advice may be suggested:
a) $F_G$ too low: further hydrolysis (GG-linkages being more stable against acid hydrolysis) or/and further washing at slightly higher pH-values (M-rich fragments more acid soluble than G-rich fragments).
b) "Wrong" $DP_n$: if the average $DP_n$ is too low, the yield will be reduced due to an increased loss when filtering through the 1 kDa filter. The yield can however be increased when the average $DP_n$ is too high; here, an increased acid hydrolysis will result in more molecules being within the desired parameter range.

EXAMPLE 4

Solutions for Administration

Inhalation solutions are prepared by dissolving sodium oligoguluronates of $DP_n$ 5 to 18 or 7 to 15 prepared according to Examples 1 and 2 respectively in sterile water for injections at concentrations of 6, 8 and 10% wt.

Aliquots of these are then loaded into a spray applicator for administration to the lungs in doses of 1 to 5 mL, preferably 2-3 mL.

Further aliquots are loaded into bottles with caps carrying droppers. Drops may be administered into the nose or ears, e.g. 2-4 drops per ear or nostril.

EXAMPLE 5

Vaginal Gel

Sodium oligoguluronates prepared according to Examples 1 and 2 are mixed in to a commercial vaginal lubricant gel (e.g. K-Y Jelly (from Johnson & Johnson) or Astroglide (from BioFilm Inc)) at concentrations of 5 and 15% wt. The gel is applied liberally, preferably 2-4 hours before insemination or intercourse.

EXAMPLE 7

Effect on Mucin

Sputum samples were collected from chronic obstructive pulmonary disease (COPD) patients. The samples were gently stirred, divided into portions, frozen and stored at −40° C.

Control and mixed samples (sputum and G-block) were gently stirred for 1 min, de-gassed at approx 10 mBar for 2×1 minute and subsequently placed into the fridge for 5 min before they were transferred to the rheometer for testing.

Rheological measurements of the pure and mixed COPD sputum was carried out on plate/cone (40 mm/1° or 25 mm/1°, depending on the quantity of the sample) using a Rheologica Stress-Tech general purpose rheometer at 10° C. to minimize the effect of any proteolytic enzymes present.

The rheological characterisation of the pure COPD sputum and sputum mixed with G-blocks was performed in four different steps:

1. Oscillating strain control for 2 min with constant strain 0.03 and frequency at 1 Hz.
2. Oscillating strain control after pre-shear (1 min at 20 s$^{-1}$ shear rate) for 60 min with constant strain at 0.03 and frequency at 1 Hz.
3. Frequency sweep with range from 0.01-5 Hz at constant strain 0.03.
4. Stress sweep with range from 0.02-20 Pa at 1 Hz.

Treatment #2 (pre-shear and 1 hour measurement) represents the basis for the presented experimental results. This treatment was repeated 2-3 times within 0-24 hrs.

Results from three ex vivo COPD sputum samples are reported here. They have been reologically tested "as such" (control) as well as being dosed with addition of G-blocks:
  pure sputum (control)
  sputum+75 microliters 150 mg/ml (per 0.5 g sputum sample) of Sodium guluronate oligomers DP10

The sodium guluronate oligomer DP 10 had the following characteristics:
$F_G$ 0.79, $F_M$ 0.11, $F_{GG}$ 0.76, $F_{GM}=F_{MG}$ 0.03, $F_{MM}$ 0.07, $F_{MGG}=F_{GGM}$ 0.02, $F_{MGM}$ 0.01, $F_{GGG}$ 0.74, $F_G$(red) 0.10, $F_G$(tot) 0.89, $DP_n$ 10

Figure 1A:
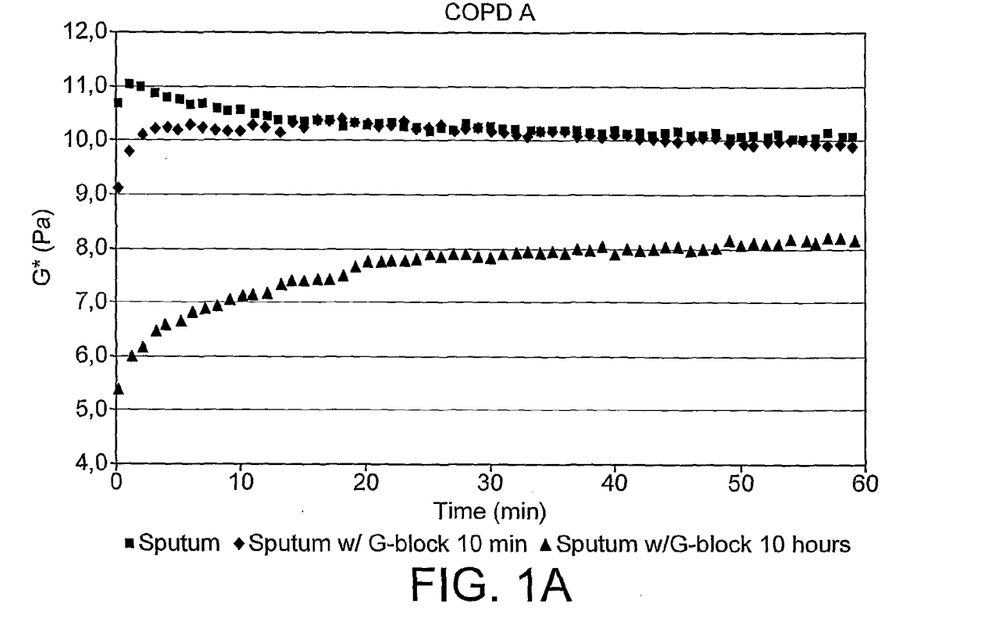
FIGS. 1*a* and 1*b*, 2*a* and 2*b*, and 3*a* and 3*b* show changes in G* (top) and η* (bottom) in sputum from a COPD patient with time and as function of added oligouronate.
Figure 1B:
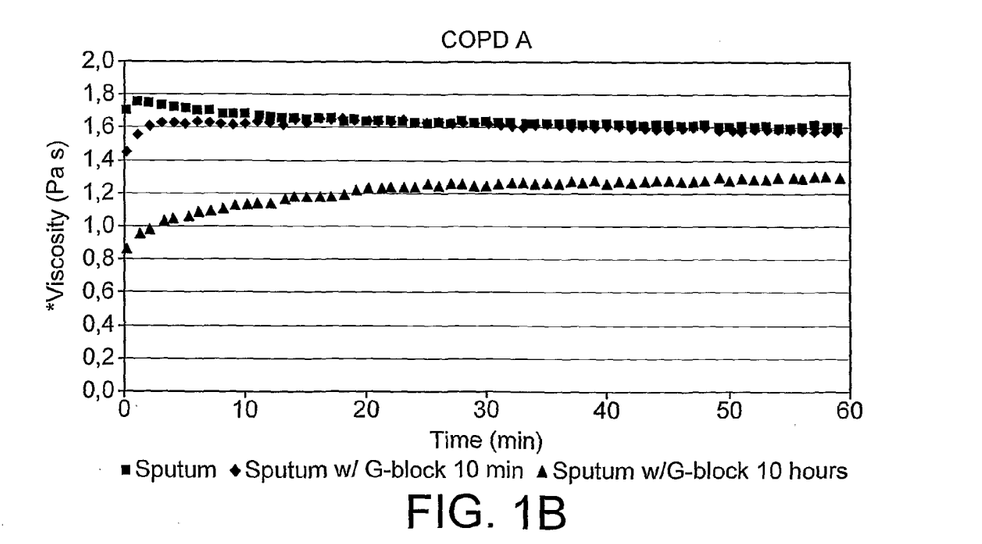
Figure 2A:
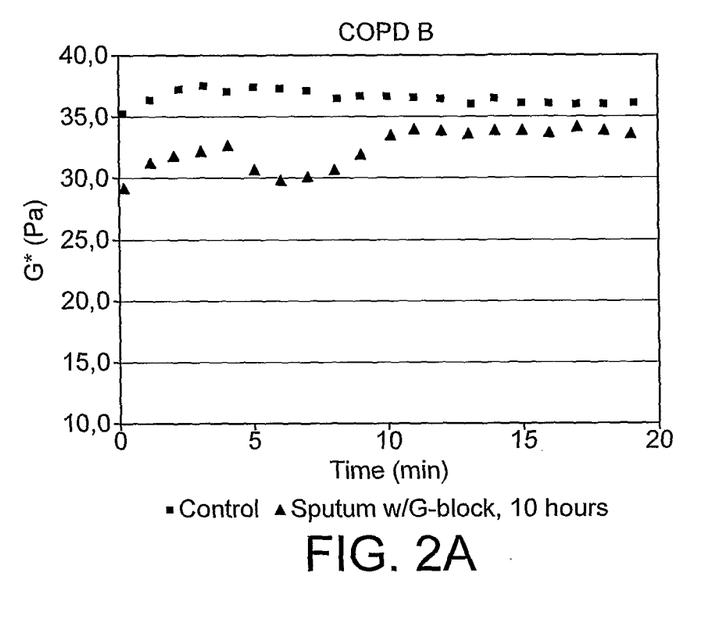
Figure 2B:
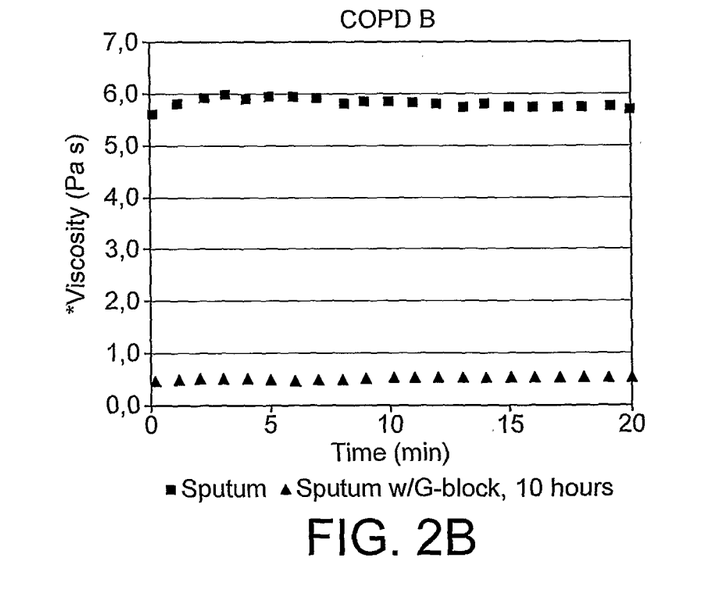
Figure 3A:
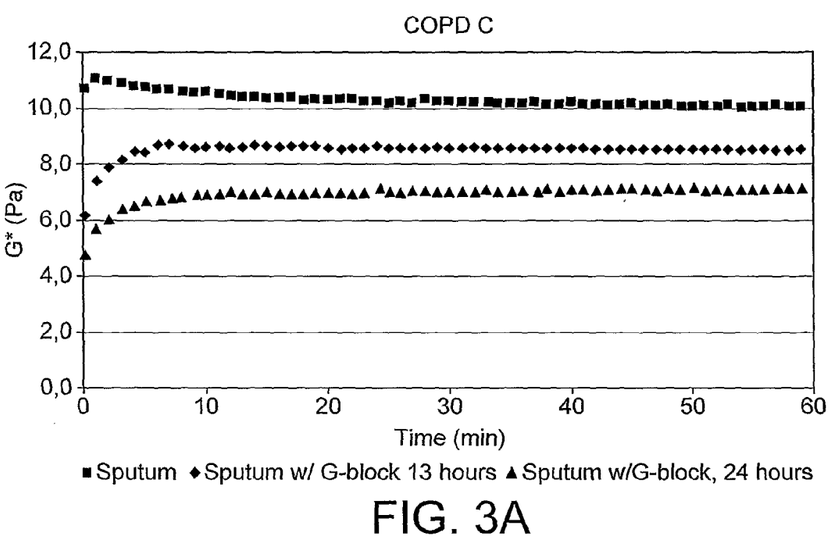
Figure 3B:
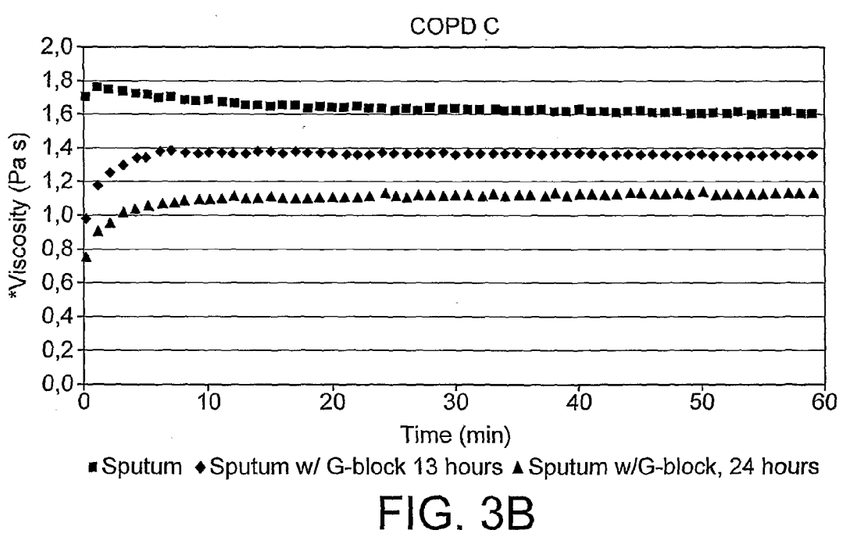

FIGS. 1a, 2a and 3a show the development of the complex modulus (G*) for the COPD sputum samples (with and without oligouronate) after the end of the pre-shear treatment and at given time-spans after the introduction of the oligouronate. FIGS. 1b, 2b and 3b show the development of the complex viscosity of the same sputum sample as in FIGS. 1a, 2a and 3a.

Addition of oligouronate obviously and over time reduces the mechanical properties of COPD sputum ex vivo. Both the complex dynamic modulus as well as the complex dynamic viscosity is considerably reduced. The change in the phase angle is, however, not effected to such an extent as G* and eta* (data not included). This is most important since it clearly shows that the mechanical properties of the mucin network is preserved.

EXAMPLE 8

Ferning

Mucin compositions were prepared as follows:
a) 18 mg mucin per mL 0.05M aqueous NaCl;
b) 18 mg mucin and 1 mg alginate per mL 0.05M aqueous NaCl; and
c) 18 mg mucin and 0.5 mg guluronate oligomer ($DP_n$=10, as in Example 7) per mL 0.05M NaCl The compositions were air dried and photomicrographs were recorded. These (not included here) clearly showed that the guluronate oligomer promoted ferning.

EXAMPLE 9

Mechanical Properties of Mucus

Figure 4:
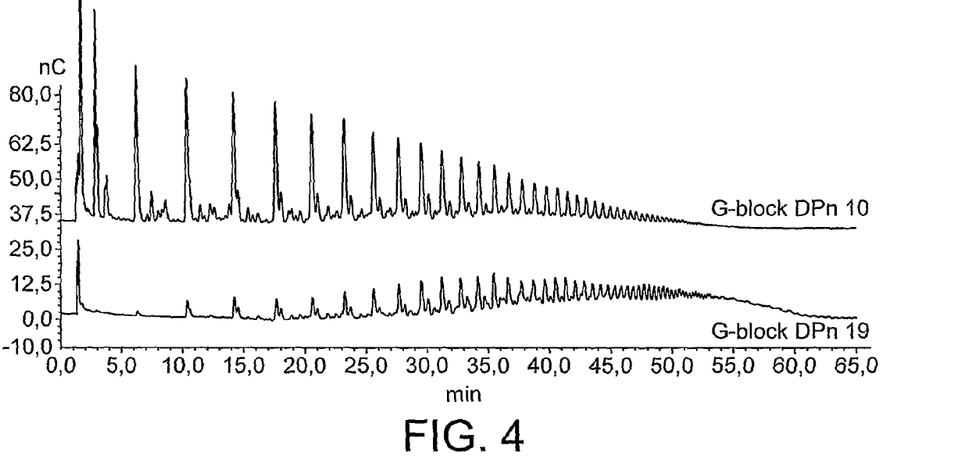
FIG. 4 is a Dionex chromatogram of the $DP_n$ 10 G-block material used in Example 7 and, by way of comparison the precursor $DP_n$ 19 material from which the high molecular weight tail has not been removed.
Figure 5:
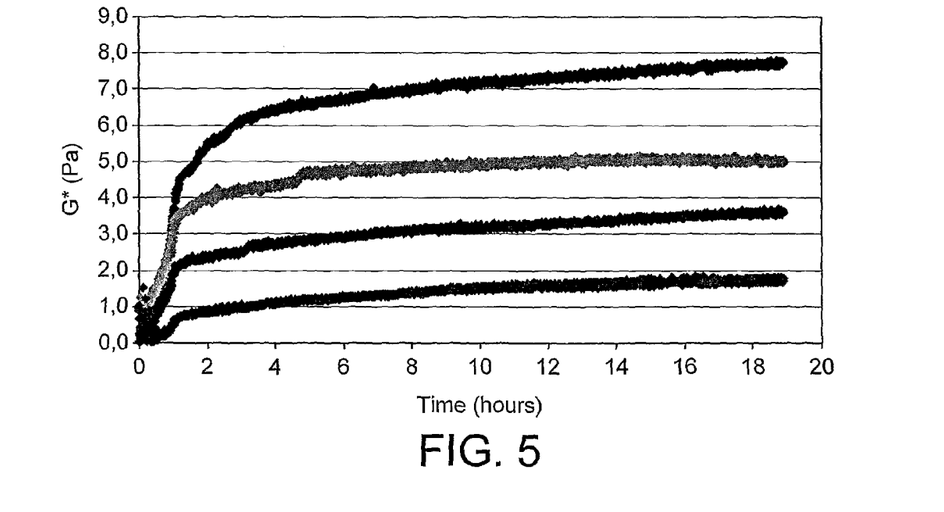
FIG. 5 shows the development over time of the mechanical properties of a model mucus in the presence of the G-block materials of FIG. 4.

Two model mucus materials were prepared, the first 18 mg/mL mucin and 0.6 mg/mL alginate in water, the second only 18 mg/mL mucin. 4 mg/mL G-block $DP_n$=10 (as Example 7) or $DP_n$=19 were added to each and the development of the dynamic complex modulus G* over time was recorded for each sample. G* is indicative of the mechanical properties of the mucus. The results are set out in FIG. 5: from the top mucin/alginate; mucin; mucin/alginate plus $DP_n$ 19; and mucin/alginate plus $DP_n$ 10. As can be seen, the $DP_n$ 10 G-block, which lacks the high molecular weight tail, reduces the solid-like behaviour of the mucus more than the $DP_n$ 19 G-block. FIG. 4 is a Dionex chromatogram for the two G-blocks used. As can be seen, the $DP_n$ 19 sample has a shoulder to the far right indicating the presence of the high molecular weight tail.

EXAMPLE 10

Etanercept Composition $DP_n$=10 G-block (as Example 7) is dissolved at 40 mg/mL in 50 mg/mL etanercept aqueous solution for injections (available under the Registered Trade Mark Enbrel from Amgen, CA, USA).

EXAMPLE 11

Infliximab Composition $DP_n$=10 G-block 8 mg/mL (as Example 7) and infliximab 10 mg/mL (available from Centocor, PA, USA under the Registered Trade Mark Remicade) are dissolved in sterile water.

EXAMPLE 12

Rituximab Composition $DP_n$=10 G-block (as Example 7) is dissolved at 10 mg/mL in 10 mg/mL rituximab aqueous solution for injections (available under the Registered Trade Mark Rituxan from Genentech, CA, USA).

EXAMPLE 13

Erythropoietin Composition $DP_n$=10 G-block (as Example 7) is dissolved at 8 mg/mL in 4000 U/mL epoetin alfa aqueous solution for injections (available under the Registered Trade Mark Epogen from Amgen, CA, USA).

EXAMPLE 14

G-CSF Composition $DP_n$=10 G-block (as Example 7) is dissolved at 9 mg/mL in 10 mg/mL pegfilgrastin aqueous solution for injections (available under the Registered Trade Mark Neulasta from Amgen, CA, USA).

EXAMPLE 15

Trastuzumab Composition $DP_n$=10 G-block (as Example 7) is dissolved at 15 mg/mL and trastuzumab (available under the Registered Trade Mark Herceptin from Genentech, CA, USA) at 22 mg/mL in bacteriostatic water for injections.

EXAMPLE 16

Interferon Composition $DP_n$=10 G-block (as Example 7) is dissolved at 1 mg/mL in 30 microgram/mL interfeon beta-1a aqueous solution for injections (available under the Registered Trade Mark Avonex from Biogen Idec, Hoofddorp, NL).

EXAMPLE 17

Insulin Composition $DP_n=10$ G-block (as Example 7) is dissolved at 10 mg/mL in 100 U/mL insulin aqueous solution for injections (available under the Registered Trade Mark Humulin from Ely Lilly, IN, USA).

The compositions of Examples 10 to 17 may typically be administered nasally, vaginally or sub-lingually, generally at dosages of the order of magnitude recommended by the suppliers of the commercially available drug compounds referred to in these Examples.

The invention claimed is:

1. A pharmaceutical composition comprising:
    (a) a physiologically tolerable oligouronate comprising guluronate or galacturonate residues and comprising:
        (i) a guluronate or galacturonate molar fraction ($F_G$) of at least 0.85,
        (ii) a mannuronate molar fraction ($F_M$) of no more than 0.15,
        (iii) a number average degree of polymerization in the range 7 to 15, and
        (iv) at least 95% mole with a degree of polymerization less than 17; and
    (b) a macromolecular drug that is different from the oligouronate in (a) having a molecular weight above 2000 Da.

2. The composition of claim 1, where the oligouronate comprising guluronate or galacturonate residues comprises:
    (i) a guluronate or galacturonate molar fraction ($F_G$) of at least 0.92, and
    (ii) a mannuronate molar fraction ($F_M$) of no more than 0.08.

3. A method of enhancing uptake of a macromolecular drug across a mucosal surface in a human or non-human vertebrate subject comprising administering to the mucosal surface of said subject a pharmaceutical composition according to claim 1, wherein uptake of said macromolecular drug across said mucosal surface is enhanced.

4. A method of treatment of a human or non-human vertebrate subject to reduce mucosal viscosity on a mucosal surface in said subject comprising applying to said mucosal surface an effective amount of a pharmaceutical composition according to claim 1, wherein the oligouronate comprising guluronate or galacturonate residues comprises:
    (i) a guluronate (or galacturonate) molar fraction ($F_G$) of at least 0.92, and
    (ii) a mannuronate molar fraction ($F_M$) of no more than 0.08,
wherein the mucosal viscosity on the mucosal surface of the subject is reduced.

5. A sterile sprayable aqueous liquid composition comprising an aqueous solution of a physiologically tolerable oligouronate comprising guluronate or galacturonate residues, said oligouronate comprising guluronate or galacturonate residues comprising:
    (i) a guluronate or galacturonate molar fraction ($F_G$) of at least 0.85,
    (ii) a mannuronate molar fraction ($F_M$) of no more than 0.15,
    (iii) a number average degree of polymerization in the range 7 to 15, and
    (iv) at least 95% mole with a degree of polymerization less than 17,
wherein said oligoguluronate or oligogalacturonate is in the aqueous solution at a concentration of 40 to 140 mg/mL, and wherein said concentration is calculated on the basis of the weight of the oligoguluronate or oligogalacturonate in sodium salt form.

6. The sterile sprayable aqueous liquid composition as claimed in claim 5, wherein said oligouronate comprising guluronate or galacturonate residues comprises:
    (i) a guluronate or galacturonate molar fraction ($F_G$) of at least 0.92, and
    (ii) a mannuronate molar fraction ($F_M$) of no more than 0.08.

7. A spray applicator comprising a reservoir and a droplet generator, said reservoir containing the sterile sprayable aqueous liquid composition according to claim 5.

8. A method of treatment of a human or non-human vertebrate subject to reduce mucosal viscosity on a mucosal surface in said subject comprising applying to said mucosal surface an effective amount of a composition according to claim 5.

9. A method of treatment of a human or non-human vertebrate animal subject to reduce mucosal viscosity on a mucosal surface therein comprising administering to said surface an effective amount of a physiologically tolerable oligouronate comprising guluronate or galacturonate residues comprising:
    (i) a guluronate or galacturonate molar fraction ($F_G$) of at least 0.92,
    (ii) a mannuronate molar fraction ($F_M$) of no more than 0.08,
    (iii) a number average degree of polymerization in the range 7 to 15, and
    (iv) at least 95% mole with a degree of polymerization less than 17.

10. A method of treatment of a human or non-human vertebrate animal subject to reduce mucosal viscosity on a mucosal surface therein comprising administering to said surface an effective amount of a composition according to claim 6.

11. A method of enhancing uptake of a drug substance across a mucosal surface in a human or non-human vertebrate animal subject comprising administering to the mucosal surface of said subject a drug substance with a physiologically tolerable oligouronate comprising guluronate or galacturonate residues comprising:
    (i) a guluronate or galacturonate molar fraction ($F_G$) of at least 0.92,
    (ii) a mannuronate molar fraction ($F_M$) of no more than 0.08,
    (iii) a number average degree of polymerization in the range 7 to 15, and
    (iv) at least 95% mole with a degree of polymerization less than 17,
wherein uptake of said drug substance across said mucosal surface is enhanced.

12. The composition of claim 1, wherein the macromolecular drug is selected from the group consisting of nucleic acids, proteins, peptides, glycoproteins, hormones and antibodies.

13. The composition of claim 1, wherein said oligouronate comprising guluronate or galacturonate residues has a range of degrees of polymerization.

14. The composition of claim 1, wherein said oligouronate comprising guluronate or galacturonate residues is obtained by acid hydrolysis.

15. The sterile sprayable aqueous liquid composition of claim 5, wherein said oligouronate comprising guluronate or galacturonate residues has a range of degrees of polymerization.

16. The sterile sprayable aqueous liquid composition of claim 5, wherein said oligouronate comprising guluronate or galacturonate residues is obtained by acid hydrolysis.

* * * * *